(12) United States Patent
Musunuri et al.

(10) Patent No.: US 7,276,359 B1
(45) Date of Patent: Oct. 2, 2007

(54) POLYNUCLEOTIDE COMPOSITION, METHOD OF PREPARATION, AND USE THEREOF

(75) Inventors: Shankar Musunuri, Downingtown, PA (US); Patrick P. DeLuca, Lexington, KY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/622,235

(22) PCT Filed: Mar. 12, 1999

(86) PCT No.: PCT/US99/05547

§ 371 (c)(1), (2), (4) Date: Aug. 14, 2000

(87) PCT Pub. No.: WO99/45966

PCT Pub. Date: Sep. 16, 1999

Related U.S. Application Data (60) Provisional application No. 60/078,080, filed on Mar. 13, 1998.

(51) Int. Cl.
C12N 15/64 (2006.01)
A61K 31/70 (2006.01)

(52) U.S. Cl. .................................. 435/91.4; 435/320.1

(58) Field of Classification Search .................. 514/44; 536/23.1; 435/455, 320.1; 264/5
See application file for complete search history.

(56) References Cited

U.S. PATENT DOCUMENTS 5,661,022 A * 8/1997 Kotani et al. ................ 435/239
5,811,406 A * 9/1998 Szoka et al. .................... 514/44
5,981,182 A * 11/1999 Jacobs, Jr. et al. .............. 435/6

FOREIGN PATENT DOCUMENTS

| WO | WO93/00807 | 1/1993 |
|---|---|---|
| WO | WO95/27721 | 10/1995 |
| WO | WO96/27393 | 9/1996 |
| WO | WO96/41873 | 12/1996 |
| WO | WO97/10851 | * 3/1997 |
| WO | WO97/40839 | 11/1997 |
| WO | WO98/47490 | 10/1998 |

OTHER PUBLICATIONS

McCluskie et.al.; Route and Method of Delivery of DNA Vaccine Influence Immune Responses in Mice and Non-Human Primates, 1999, Molecular Medicine, 5: 287-300.*
Leitner et.al.; DNA and RNA-based vaccines: principles, progress and prospects, 2000, Vaccine 18: 765-777.*
Chattergoon et.al.; Genetic immunization: a new era in vaccines and immune therapeutics, 1997, FASEB J. 11: 753-763.*
Verma et.al.; Gene therapy- promises, problems and prospects, 1997, Nature, vol. 389: 239-242.*
Dang et.al.; Gene Therapy and Translational Cancer Research, 1999, Clinical Cancer Research vol. 5: 471-474.*
Kalyanasundaram et.al.; Coacerate microspheres as carriers of recombinant adenoviruses, 1999, Cancer Gene Therapy, vol. 6, No. 2: 107-112.*
Ando et.al.; In Vitro Evaluation of Biodegradable Microspheres as a vector for Gene Delivery Systems, 1999, Controlled Release Society, Inc.: 689-690.*
Talsma et al., Stabilization of gene delivery systems by freeze-drying, 1997, International Journal of Pharmaceutics, vol. 157, pp. 233-238.*

* cited by examiner

*Primary Examiner*—Quang Nguyen
(74) *Attorney, Agent, or Firm*—J. Darrell Fontenot (57) ABSTRACT

A lyophilized polynucleotide composition contains at least one polynucleotide and at least one cryoprotectant, wherein the ratio of the polynucleotide to cryoprotectant is from about 0.001 to about 1.0 part by weight polynucleotide per 1.0 part by weight of the cryoprotectant. This composition also contains from about 0.5 weight percent to about (6) weight percent water, based on the total weight of the final lyophilized polynucleotide composition. The polynucleotide composition of this invention is characterized by enhanced stability, in that it retains at least 90% supercoil over a time period of at least (10) days at a temperature of about 37° C. The lyophilized polynucleotide composition also has improved solubility. An improved process for lyophilization of polynucleotides employs a specific primary drying cycle, that results in the above-described stable, lyophilized polynucleotide composition.

28 Claims, 2 Drawing Sheets

POLYNUCLEOTIDE COMPOSITION, METHOD OF PREPARATION, AND USE THEREOF

CROSS-REFERENCE TO RELATED APPLICATIONS

This is a 371 of PCT/US99/05547, which claims the benefit of the priority of U.S. Patent Application No. 60/078,080, filed Mar. 13, 1998.

FIELD OF THE INVENTION

The present invention relates to a polynucleotide composition that has improved stability. The present invention also relates to a process for preparing the polynucleotide composition through lyophilization.

BACKGROUND OF THE INVENTION

Polynucleotide compositions have a variety of uses in the industrial, pharmaceutical, medical, nutritional, and/or agricultural fields. As one example, polynucleotides are useful for the production of proteins useful in these fields. Furthermore, polynucleotides are useful themselves as in vivo reagents, in diagnostic/imaging protocols, as reagents in gene therapy, in antisense protocols and in vaccine applications or otherwise as pharmaceuticals used to treat or prevent a variety of ailments such as genetic defects, infectious diseases, cancer, and autoimmune diseases. Polynucleotides are also useful as in vitro reagents in assays such as biological research assays, medical, diagnostic and screening assays and contamination detection assays. For each above-mentioned utility, the polynucleotides, such as plasmid DNA, must be retained for extended periods of time, preferably at unrefrigerated or unfrozen temperatures. A problem which has hindered the development of polynucleotides for such uses is that the polynucleotides tend to be unstable when unfrozen. For example, polynucleotides have been found to decrease in activity when left in solution for longer than a few hours.

A desirable method for measuring the stability of polynucleotides is the loss of supercoil (or "SC") of the polynucleotides over time. The term "supercoil" is defined as the physical state of a polynucleotide in which one strand of the polynucleotide is underwound or overwound in relation to other strands of the polynucleotide. The loss of supercoil over time has the undesirable effect of reducing the purity of a polynucleotide composition. Therefore, many attempts have been made to address this problem and improve the stability of polynucleotides. One such attempt includes a polynucleotide preparative method involving precipitation followed by drying. However, such methods have not achieved desired polynucleotide stabilities. Other attempts in the prior art include storing polynucleotides in salt solutions; however, these methods also lead to a loss of supercoil structure.

Another method for stabilizing polynucleotides involves lyophilizing the polynucleotides. Lyophilization, also referred to as freeze drying, has been used in the past to stabilize or preserve such items as food, blood plasma, vital organs, proteins, intact cells such as bacterial and unicellular eukaryotic organisms, and biologically active substances such as drugs. The process of lyophilization includes dissolving the material to be lyophilized in a solvent, usually water, and freezing the solution. A cryoprotectant amount is frequently included to stabilized the polynucleotide. After freezing the solution, vacuum is applied and the frozen material is gradually heated to sublime the solvent from the frozen state. The final freeze-dried material is typically recovered as a cake of the same shape and size as the frozen material and is of sufficient porosity to permit reconstitution. In the early 1980's, the American Type Culture Collection, for example, sold lyophilized DNA stabilized with the cryoprotectant, lactose.

PCT Application No. WO96/41873, published Dec. 27, 1996, and its related U.S. Pat. No. 5,811,406, issued Sep. 22, 1998, which are incorporated herein by reference, disclose stabilizing a polynucleotide complex that contains a cryoprotectant by lyophilizing the complex in an undisclosed manner. However, the process parameters of lyophilization can have a significant impact on the stability and the solubility of a polynucleotide composition. The lyophilization process can result in the polynucleotides having low solubility, requiring that more solvent be used to permit reconstitution. These documents fail to address these issues of lyophilization and thus fail to teach any methods of providing lyophilized compositions with enhanced stability or solubility.

There remains a need in the art for polynucleotide compositions characterized by enhanced stability, particularly for pharmaceutical uses, as well as for methods for producing such stable polynucleotide compositions.

SUMMARY OF THE INVENTION

In one aspect, the present invention provides a lyophilized polynucleotide composition comprising at least one polynucleotide and at least one cryoprotectant, wherein the ratio of the polynucleotide to cryoprotectant is from about 0.001 to about 1.0 part by weight polynucleotide per 1.0 part by weight of the cryoprotectant. This composition also comprises from about 0.5 weight percent to about 6 weight percent water, based on the total weight of the final lyophilized polynucleotide composition. The polynucleotide composition of this invention is characterized by enhanced stability, in that it retains at least 90% supercoil over a time period of at least 10 days at a temperature of about 37° C.

In another aspect, the present invention provides a method for preparing a lyophilized polynucleotide composition characterized by enhanced stability. The steps of this method include subjecting a polynucleotide solution containing a cryoprotectant, which composition has been cooled until frozen and subjected to a vacuum, to a primary drying cycle which comprises gradually heating the polynucleotide solution at a temperature of from about −20° C. to about 20° C. over a period of from about 5 to about 30 hours, while avoiding liquification (also referred to as "melt back") of the composition. This primary drying cycle reduces the time necessary for the complete lyophilization process and provides the resulting lyophilized polynucleotide in a substantially amorphous physical structure which retains at least 90% supercoil over a time period of at least 10 days at a temperature of about 37° C. This product may then be reconstituted in an aqueous solution, if desired.

In a further aspect, the present invention provides a lyophilization method with parameters designed to provide a lyophilized polynucleotide composition which is characterized by enhanced stability and enhanced solubility. This method comprises the steps of:

(a) forming an aqueous polynucleotide solution having a pH of from about 6.2 to about 7.8 and comprising from about 0.1 mg/mL to about 5 mg/mL of at least one polynucleotide based on the total volume of the polynucleotide solution, and from about 0.5 weight percent to about 10 weight percent of at least one cryoprotectant, based on the total weight of the polynucleotide solution;

(b) cooling the polynucleotide solution to a temperature of from about −30° C. to about −70° C., until frozen;

(c) applying vacuum to reduce the pressure to about 25 mTorr to about 250 mTorr;

(d) gradually heating the polynucleotide solution a first time to a temperature of from about −40° C. to about 20° C. over a period of from about 5 hours to about 40 hours;

(e) holding the polynucleotide solution after heating step (d), at a temperature of from about −35° C. to about 10° C. and at a pressure of from 25 mTorr to about 250 mTorr for a period of from about 1 hour to about 10 hours;

(f) gradually heating the polynucleotide solution after the holding step (e), to a temperature of from about 20° C. to about 35° C. over a period of from about 1 hour to about 20 hours and at a pressure of from about 25 mTorr to about 150 mTorr; and (g) recovering a lyophilized polynucleotide composition having a water content of from about 0.5 weight percent to about 6 weight percent based on the total weight of the recovered composition.

In another aspect, the present invention provides a lyophilized composition produced by the methods above.

In still another aspect, the present invention also provides a liquid polynucleotide composition which comprises the lyophilized composition described above, reconstituted in water and characterized by a pH of between about 6.2 to about 7.8.

In yet a further aspect, the invention provides a pharmaceutical composition which comprises an active ingredient, which is a lyophilized composition as described above or a reconstituted liquid composition, as described above. These ingredients are desirably combined with a pharmaceutically acceptable excipient or carrier.

In still another aspect, the present invention provides a method of treating a mammalian subject by administering to the subject an effective amount of the pharmaceutical composition. Such administration may be by any conventional route of administration, e.g., oral, parentaral, intranasal or intra-pulmonary.

Other aspects and advantages of the present invention are described further in the following detailed description of the preferred embodiments thereof.

DETAILED DESCRIPTION OF THE INVENTION

The present invention addresses the need in the art by providing, as described herein, a polynucleotide composition that has improved stability, a polynucleotide composition that has improved solubility, and a process for lyophilization that results in a stabilized polynucleotide composition.

I. The Polynucleotide Composition of the Present Invention

The "polynucleotide composition" of the present invention refers to the polynucleotide mixture that has increased stability and solubility over polynucleotide mixtures of the prior art. Preferably, the polynucleotide composition of this invention is typically a powder having a predominantly amorphous structure, with only minor amounts of a crystalline structure, and is produced by subjecting a polynucleotide solution to a novel lyophilization process described herein.

A. The Polynucleotide Solution

The term "polynucleotide solution" as used hereinafter refers to an aqueous polynucleotide mixture prior to lyophilization. The polynucleotide solution that is lyophilized is an aqueous mixture of at least one polynucleotide and at least one cryoprotectant. Preferably, the ratio of polynucleotide to cryoprotectant in the polynucleotide solution is from about 0.001 to about 1.0 part by weight polynucleotide per 1.0 part by weight cryoprotectant. The polynucleotide solution may also contain optional non-aqueous solvent(s) and other additives. The concentration of the polynucleotide, cryoprotectant, solvent (including water) and optional additives are adjusted so that an adequate mass of polynucleotide is lyophilized and so that the polynucleotide is not significantly degraded during lyophilization.

1. The Polynucleotide

Any polynucleotide, including any modified polynucleotide, may be used in the present invention. Suitable polynucleotides include, for example, BDNA, ADNA, ZDNA, RNA, tRNA, and mRNA. The polynucleotide may also be in any form. For example, the polynucleotide may be circular, or linear. The polynucleotide may contain one or more strands. For example, a single stranded DNA or RNA, a double stranded DNA, a double stranded DNA-RNA hybrid, or a triple or quadrupled stranded polynucleotide may be used. Examples of double stranded DNA include, inter alia, chromosomal DNA, R Factor, PCR products, plasmid DNA, bacteriophage, viral RNA and DNA vectors, including, among others, alphavirus, adenovirus, vaccinia, retrovirus, adeno-associated virus, positive and negative stranded RNA viruses, herpes viruses, and viroids, delta virus and poliovirus. DNA preferably includes coding sequences that encode proteins, preferably operably linked to regulatory elements, genes including operator control and termination regions, and self replicating systems such as plasmid DNA. Single-stranded polynucleotides include antisense polynucleotides, ribozymes and triplex-forming oligonucleotides. The polynucleotides may be modified as thioates, phosphorothioates, and phosphonates, etc. For single-stranded polynucleotides in compositions of the invention which are intended for pharmaceutical use, it is preferable to prepare a complementary or "linker strand" to the therapeutic strand as part of the polynucleotide composition. The linker strand may be a separate strand, or it may be covalently attached to or an extension of the therapeutic strand so that the therapeutic strand essentially doubles back and hybridizes to itself. Alternatively, the linker strand may have a number of arms that are complementary so that it hybridizes to a plurality of polynucleotide strands.

In preferred embodiments, the polynucleotide is supercoiled plasmid DNA which is an expression vector that encodes an immunogen operably linked to regulatory elements which are functional in human cells. In some preferred embodiments the immunogen encoded by the coding sequence is a protein from a pathogen such as herpes simplex virus $gD_2$ protein or human immunodeficiency virus proteins, such as those encoded by HIV-1 gag, pol or emv genes. The coding sequences are operably linked to a suitable promoter, such as a cytomegalovirus (CMV) intermediate early promoter, and an SV40 polyadenylation signal. For example, U.S. Pat. No. 5,593,972, which is incorporated herein by reference, describes plasmids useful in the present invention.

The polynucleotide may comprise naked polynucleotide such as plasmid DNA, multiple copies of the polynucleotide or different polynucleotides, or may comprise a polynucleotide associated with a "co-agent", such as a local anaesthetic, a peptide, a lipid including cationic lipids, a liposome or lipidic particle, a polycation such as polylysine, a branched, three-dimensional polycation such as a dendrimer, a carbohydrate, cationic amphiphiles, detergents, benzylammonium surfactant, or other compounds that facilitate polynucleotide transfer to cells. Non-exclusive examples of co-agents useful in this invention are described in U.S. Pat. Nos. 5,593,972; 5,703,055; 5,739,118; 5,837,533 and International Patent Application No. WO96/10038, published Apr. 4, 1996; and International Patent Application No WO94/16737, published Aug. 8, 1994, which are each incorporated herein by reference. When the agent used is a local anesthetic, preferably bupivacaine, an amount of from about 0.1 weight percent to about 1.0 weight percent based on the total weight of the polynucleotide solution is preferred. See, also, International Patent Application No. PCT/US98/22841, which teaches the incorporation of benzylammonium surfactants as co-agents, administered in an amount of between about 0.001-0.03 weight %, the teaching of which is hereby incorporated by reference.

Also, for use as a polynucleotide in the solutions of this invention, the polynucleotide base, carbohydrate, or linkage may be modified according to techniques well known to those skilled in the art.

Preferably, the polynucleotide is present in the polynucleotide solution at a concentration of from about 0.1 mg/mL to about 5.0 mg/mL. In some other embodiments, the polynucleotide is present in the solution at a concentration of from about 1.0 mg/mL to about 3.0 mg/mL. In still other embodiments, the polynucleotide is present in the solution at a concentration of from about 1.0 mg/mL to about 2.0 mg/mL.

2. Cryoprotectant(s)

The term "cryoprotectant" may be used interchangeably with the term "lyoprotectant" and is intended to refer to single cryoprotectants and lyoprotectants, as well as mixtures of two or more cryoprotectant compounds. A cryoprotectant may be any compound that stabilizes the polynucleotide during and after lyophilization. A variety of cryoprotectants are described in conventional texts, such as Remington: The Science and Practice of Pharmacy, Vol. 2, $19^{th}$ edition (1995).

In one embodiment, the cryoprotectant useful in the present invention is a sugar alcohol, such as alditol, mannitol, sorbitol, inositol, polyethylene glycol and combinations thereof. Particularly desirable is polyethylene glycol. In another embodiment, the cryoprotectant is a sugar acid, including an aldonic acid, an uronic acid, an aldaric acid, and combinations thereof The cryoprotectant of this invention may also be a carbohydrate. Suitable carbohydrates are aldehyde or ketone compounds containing two or more hydroxyl groups. The carbohydrates may be cyclic or linear and include for example aldoses, ketoses, amino sugars, alditols, inositols, aldonic acids, uronic acids, or aldaric acids, or combinations thereof. The carbohydrate may also be a mono-, a di-, or poly-, carbohydrate, such as for example, a disaccharide or polysaccharide. Suitable carbohydrates include for example, glyceraldehyde, arabinose, lyxose, pentose, ribose, xylose, galactose, glucose, hexose, idose, mannose, talose, heptose, glucose, fructose, gluconic acid, sorbitol, lactose, mannitol, methyl α-glucopyranoside, maltose, isoascorbic acid, ascorbic acid, lactone, sorbose, glucaric acid, erythrose, threose, arabinose, allose, altrose, gulose, idose, talose, erythrulose, ribulose, xylulose, psicose, tagatose, glucuronic acid, gluconic acid, glucaric acid, galacturonic acid, mannuronic acid, glucosamine, galactosamine, sucrose, trehalose or neuraminic acid, or derivatives thereof. Suitable polycarbohydrates include for example arabinans, fructans, fucans, galactans, galacturonans, glucans, mannans, xylans (such as, for example, insulin), levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, or starch. Among particularly useful carbohydrates are sucrose, glucose, lactose, trehalose, and combinations thereof. Sucrose is a particularly useful cryoprotectant.

Preferably, the cryoprotectant of the present invention is a carbohydrate or "sugar" alcohol, which may be a polyhydric alcohol. Polyhydric compounds are compounds that contain more than one hydroxyl group. Preferably, the polyhydric compounds are linear. Suitable polyhydric compounds include for example glycols such as ethylene glycol, polyethylene glycol, and polypropylene glycol; glycerol; or pentaerythritol; or combinations thereof.

In some preferred embodiments, the cryoprotectant agent is sucrose, trehalose, mannitol, or sorbitol. In other preferred embodiments, the cryoprotectant agent is sucrose. Any of these cryoprotectants made be formed in admixture with at least one of the others, as desired.

The cryoprotectant or mixture of cryoprotectants is preferably present in the polynucleotide solution at a concentration of from about 0.5 weight percent to about 10 weight percent. In some embodiments, the cryoprotectant(s) is present in the solution at a concentration of from about 1.0 weight percent to about 8.0 weight percent. In still other embodiments, the cryoprotectant(s) is present in the solution at a concentration of from about 1.0 weight percent to about 5.0 weight percent.

3. Optional Additives in the Polynucleotide Solution

The polynucleotide solution is preferably aqueous based. However, if desired, one or more solvents may be added to the solution that are compatible with the water, the polynucleotide and cryoprotectant. For example, water soluble alcohols, such as ethylene glycol, propylene glycol, or glycerol may be added to the solution.

The polynucleotide solution is preferably prepared with a buffer, so that upon rehydration of the lyophilized polynucleotide composition, isotonicity can be achieved. The polynucleotide solution preferably has a pH of from about 6.2 to about 7.8. In one embodiment, the polynucleotide solution has a pH of from about 6.2 to about 7.4. In another embodiment, the polynucleotide solution of the present invention has a pH of preferably from about 6.2 to about 6.9. This pH range aids in preventing the polynucleotide from degrading during the lyophilization method of the present invention. Therefore, buffers which may be used include any compound capable of maintaining the above-mentioned desired pH during lyophilization. Preferred buffers include phosphate and citrate, generally at a concentration of 5-60 mM. Preferably, the buffers are used at a level of from about 0.1 weight percent to about 1.2 weight percent based on the total weight of the polynucleotide solution.

Other optional additives such as facilitators (as described above), surfactants, or salts or combinations thereof may be added to the polynucleotide solution. Salts may be added to adjust the isotonicity of the polynucleotide solution. For example, salts such as sodium chloride may be used. Preferably, the salt is used in an amount of from about 0.1 weight percent to about 1.0 weight percent based on the total weight of the polynucleotide solution.

Overall these optional additives preferably comprise from about 0.1 weight percent to about 3 weight percent based on the total weight percent of the polynucleotide solution:

The polynucleotide solution formed by combining these components is then subjected to the lyophilization process of the present invention, which results in a lyophilized polynucleotide composition of this invention.

B. The Lyophilized Composition

The lyophilized polynucleotide composition of this invention prepared from the polynucleotide solution described above, thus comprises:

(a) at least one polynucleotide, (b) at least one cryoprotectant, wherein the ratio of polynucleotide to cryoprotectant is from about 0.001 to about 1.0 part by weight polynucleotide per 1.0 part by weight cryoprotectant, and (c) from about 0.5 weight percent to about 6 weight percent water, based on the total weight of the polynucleotide composition.

This lyophilized polynucleotide composition, in some embodiments, contains about 6% or less water. In some embodiments, the polynucleotide composition product contains about 5% or less water. In other embodiments, the lyophilized composition contains water at from about 2 weight percent to about 3 weight percent.

The polynucleotide composition of the present invention is characterized by increased stability compared to polynucleotide compositions of the prior art. Percentage of supercoil defines the level of purity of the polynucleotide. Thus, stability of a polypeptide is determined by the level of purity retained over time. By "increased or enhanced stability", it is meant that the polynucleotide retains at least 90% of its supercoil over a time period of at least 10 days at about 37° C. In some embodiments, the polynucleotide, preferably DNA, of the present invention retains at least 90% of its supercoil over at least 20 days at 37° C. More preferably, in some embodiments, the polynucleotide of the present invention retains at least 90% of its supercoil over at least 30 days at about 37° C.

In addition to stability, the polynucleotide composition of this invention preferably has increased solubility compared to other polynucleotide compositions of the prior art. By "increased solubility" it is meant that the polynucleotide composition of this invention preferably has a solubility in water at about 25° C. (i.e. room temperature) of at least 1 milligram per milliliter ("mg/mL"). Desirably, the polynucleotide composition of this invention has a solubility in water at about 25° C. of at least 2 mg/mL. In other preferred embodiments, the polynucleotide composition of this invention has a solubility in water at about 25° C. of at least 10 mg/mL. Solubilities as high as about 20 mg/mL are also possible. The increased stability and solubility of polynucleotide compositions of this invention are preferably obtained through lyophilization of a polynucleotide solution according to the methods disclosed herein.

The lyophilized composition according to this invention is also characterized by a predominantly amorphous physical structure. In some embodiments, the composition contains polynucleotide which is substantially amorphous, but also contains some minor amount or small percentage of crystalline, e.g., lattice, structure.

C. Pharmaceutical Compositions

The lyophilized polynucleotide composition may be formulated into a variety of forms for storage or for in vitro or in vivo use. Examples of in vivo uses for which the polynucleotide compositions of the invention are particularly useful include those methods of vaccination and gene therapy using plasmid DNA as described in U.S. Pat. Nos. 5,593,972; 5,703,055; 5,676,954; 5,580,859; 5,589,466; 5,739,118; and 5,837,533; International Patent Application No. WO96/41873, published Dec. 27, 1996; and International Patent Application No. WO94/16737, published Aug. 8, 1994, which are each incorporated herein by reference.

The lyophilized polynucleotide composition of this invention may be formulated into various dry or liquid forms. If desired, the dry lyophilized polynucleotide compositions of this invention may be milled, ground, or sieved to form a powder by techniques well known to those skilled in the art. For example, the lyophilized polynucleotide compositions may be converted to a powder through a granulator, jet mill, delumper, or shredder. Preferably, the polynucleotide composition has an average particle size of less than about 100 µm. If the composition is intended for pharmaceutical use via pulmonary administration, for example, a particle size of ≦10 µm is desired. In some preferred embodiments, the polynucleotide composition of the invention is prepared for administration to mammalian subjects in the form of, for example, powders, tablets, capsules, enteric coated tablets or capsules, or suppositories.

As another example, a liquid polynucleotide composition may be prepared by reconstituting the lyophilized composition in water, and/or made into liquid compositions. The reconstituted composition preferably has a pH of between about 6.2 to about 7.8, as described above for the initial polynucleotide solution.

Such dry compositions or liquid solutions are preferably used as pharmaceutical compositions. Thus, another embodiment of the present invention is a pharmaceutical composition, which comprises as an active ingredient a lyophilized composition as described herein or a reconstituted liquid composition as described herein, in combination with an optional pharmaceutically acceptable excipient or carrier. Depending on the purpose for which the pharmaceutical composition is desired, the excipient or carrier is suitable for any route of administration, such as oral, parenteral, intranasal, and intra-pulmonary. This lyophilized polynucleotide composition can be used as a starting material in association with other pharmaceutically acceptable excipients for developing powder, liquid or suspension dosage forms, including those for intranasal or pulmonary applications. See, e.g., Remington: The Science and Practice of Pharmacy, Vol. 2, 19$^{th}$ edition (1995), e.g., Chapter 95 Aerosols, the teaching of which is hereby incorporated by reference.

A preferred pharmaceutical composition employing these active agents is an enteric coated tablet. In a preferred embodiment, the polynucleotide composition is provided as an oral vaccine in an enteric coated capsule. The polynucleotide is plasmid DNA. Preferably, about 1 mg of DNA is loaded into a hard gelatin capsule such as those made by Capsugel, a division of Warner Lambert Parke-Davis. Flow lubricants such as talc, magnesium stearate may be added to the polynucleotide composition. Similarly, bulking agents such as cellulose may also be added. The gelatin capsules are enterically coated using, for example, EUDRAGIT enteric coating polymer material. According to other embodiments, the polynucleotide composition of the present invention may be used to form a powder which is administrable as an aerosol for delivering the polynucleotide to the lung. For example, the polynucleotide composition may be prepared to deliver genes useful in the treatment of a lung disease. Also, for example, a polynucleotide composition of the present invention having DNA encoding for cystic fibrosis transmembrane conductance regulator may be used as a treatment for cystic fibrosis.

D. Methods of Use

Thus, as still another embodiment of this invention, there is provided a method of treating a mammalian subject comprising administering to the subject an effective amount of the above-described pharmaceutical compositions. Depending on the purpose for which the composition is administered, these treatment methods comprise administering the composition by a desired route of administration, including, among others, oral, parenteral, intranasal, and intra-pulmonary. For example, the polynucleotide composition may be formulated into a liquid with acceptable isotonicity and applied intramuscularly, intravenously, intradermally or subcutaneously. The polynucleotide composition may also be applied through intra-nasal or intral pulmonary delivery (inhalation) of a powder. The polynucleotide composition may also be applied as a suppository to such body cavities as the vagina, rectum, and mouth. Methods employing these compositions include, inter alia, gene therapy protocols for diseases, e.g., cystic fibrosis.

II. The Lyophilization Process of this Invention

To produce the lyophilized polynucleotide compositions and pharmaceutical products of this invention, a polynucleotide solution formed as described above, is lyophilized according to carefully controlled steps that have an effect of increasing the stability and solubility of the resulting lyophilized polynucleotide composition. The device used to lyophilize the solution may be any device that permits the gradual cooling and gradual heating of the polynucleotide solution under vacuum. As used herein, "hold" or "holding" means maintaining a given temperature and/or vacuum over a period of time. "Ramp" or "ramping" means changing the temperature and/or vacuum conditions over a period of time. In lyophilization processes, some steps are holding steps and others are ramping steps.

The lyophilization process of the present invention is described in more detail below:

The aqueous polynucleotide solution having a pH of from about 6.2 to about 7.8 and comprising from about 0.1 mg/mL to about 5 mg/mL of at least one polynucleotide based on the total volume of the polynucleotide solution, and from about 0.5 weight percent to about 10 weight percent of at least one cryoprotectant, based on the total weight of the polynucleotide solution is first cooled to solidify or freeze the solution. In one embodiment, the solution is cooled to a temperature of from about −30° C. to about −70° C. In another embodiment, the solution is cooled to a temperature of from about −40° C. to about −60° C. In other embodiments, the solution is cooled to a temperature of from about −40° C. to about −50° C. This cooling step is preferably gradual and ramped, or carried out, over a period of from about 1 hour to about 5 hours, and more preferably from about 1 hour to about 3 hours. In some embodiments, the solution is cooled over a period of time of 1 hour to 2 hours. In some embodiments, the solution is cooled over a period of time of 2 hours to 3 hours. Preferably the solution is cooled at a linear rate over the desired cooling period. Although gradual cooling is preferred, it is also possible to quickly freeze (e.g., less than 10 minutes) the solution without significantly degrading the polynucleotide during lyophilization.

When the desired freezing temperature is reached, a vacuum is immediately applied, reducing the pressure to from about 25 mTorr to about 250 mTorr. In some embodiments, the vacuum reduces the pressure to from about 50 to about 100 mTorr. The composition is optionally held at this temperature and pressure for about 30 minutes to about 5 hours, preferably at least one hour. In one particularly desirable embodiment, the vacuum is applied by rapidly decreasing the pressure from about 300 mTorr to about 200 mTorr, and thereafter gradually decreasing the pressure to about 150 mTorr, and then to about 40 mTorr over a period of from about 1 hour to about 2 hours.

After cooling, the polynucleotide solution is subjected to the "primary drying or heating cycle", which contributes significantly to the performance of this method. In this primary heating step, the frozen solution is gradually heated a first time to a temperature of from about −40° C. to about 20° C. over a period of from about 5 hours to about 40 hours. In a desired embodiment, the frozen solution is gradually heated a first time to a temperature of from about −10° C. to about 20° C. over a period of from about 5 hours to about 20 hours. In another embodiment, the frozen solution is gradually heated to a temperature of from about −40° C. to about 10° C. In another embodiment, the frozen solution is gradually heated a first time to a temperature of from about −5° C. to about 5° C. over a period of from about 8 hours to about 20 hours. In a particularly preferred embodiment, the frozen solution is heated a first time to a temperature of 0° C. This primary heating step is preferably carried out over a period of from about 5 hours to 40 hours, desirably from about 5 to 20 hours, and more preferably over a period of from about 6 to 15 hours. In some embodiments, this first heating step is carried out over a period of about 10 hours.

In addition to heating the polynucleotide solution during the primary drying cycle, a vacuum is also applied to begin drying the solution. Preferably, vacuum is applied as soon as the primary heating step is started. The vacuum pressure during this heating step is preferably less than about 250 mTorr, and more preferably from about 25 to about 150 mTorr. In certain embodiments the vacuum pressure is from about 40 to about 150 mTorr. In still other embodiment, the vacuum pressure during this heating step is from about 60 mTorr to about 150 mTorr. In one desirably embodiment, the vacuum is preferably applied so that the pressure is dropped in less than 5 minutes to 200 mTorr and then reduced to the desired pressure over a period of from about 1 hour to about 2 hours.

Following the primary heating step, the polynucleotide solution is held at a constant temperature and pressure to equilibrate the polynucleotide solution. This holding step is preferably for a period of from about 1 hour to about 10 hours, and more preferably from about 2 hours to about 6 hours. Preferably the temperature during this holding step is maintained at from about −35° C. to about 10° C. In some embodiments, the temperature is maintained at from about −10° C. to about 10° C. for a period of from about 2 to about 10 hours. In other embodiments, the temperature is maintained at from about −5° C. to about 5° C. for a period of from about 5 hours to about 7 hours. In a preferred embodiment, the temperature is maintained at about 0° C. Preferably the vacuum pressure during this hold is maintained at less than about 200 mTorr and more preferably from about 25 mTorr to about 250 mTorr for a period of from about 1 hour to about 10 hours. In some embodiments, the vacuum pressure during this hold is maintained at about 40 mTorr to about 150 mTorr. In some embodiments, the vacuum pressure during this hold is maintained at about 60 mTorr to about 150 mTorr. The pressure and temperature selected is preferably that temperature and pressure which was achieved at the end of the primary heating step. The vacuum is preferably applied continuously from this holding step to the next step.

After this hold, secondary drying step is performed. The polynucleotide solution is gradually heated a second time to a temperature of from about 20° C. to about 35° C., over a period of from about 1 hour to about 20 hours and at a pressure of from about 25 mTorr to about 250 mTorr. In a desired embodiment, this secondary heating step gradually heats the solution to a temperature from about 20° C. to about 30° C. and at a pressure of from 25 mTorr to about 150 mTorr for a period of from about 1 hour to about 10 hours. In another embodiment the secondary heating raises the temperature from about 23° C. to about 27° C. over a period of from about 2 hours to about 3 hours. In a preferred secondary heating step, the temperature is raised to about 25° C. The vacuum pressure during the second heating step is preferably less than about 250 mTorr, and more preferably from about 25 to about 150 mTorr, and in some embodiments from about 40 to about 110 mTorr. This second heating step is preferably carried out over a period of from about 1 hour to about 5 hours and more preferably over a period of from about 2 to 3 hours.

In a particularly desirable embodiment of the lyophilization process of this invention, the primary heating step occurs desirably over a period of from about 7 hours to about 11 hours, the subsequent holding step occurs for a period of about 1 hour, and the secondary heating step occurs over a period of about 2 hours.

After this second heating, the polynucleotide solution may optionally be held again at a constant temperature and pressure to again equilibrate the polynucleotide solution. Preferably, this second hold is for a period of from about 1 hour to about 10 hours, and more preferably for about 2 hours to about 5 hours. In some embodiments, the second hold is from about 2 to 3 hours. Preferably the temperature during this hold is maintained at about 20° C. to about 30° C., more preferably from about 23° C. to about 27° C., and most preferably at 25° C. Preferably the vacuum pressure during this hold is maintained at less than about 150 mTorr and more preferably from about 20 mTorr to about 100 mTorr. The pressure and temperature selected is preferably that temperature and pressure which was achieved at the end of the second heating step.

In a preferred embodiment, the primary heating step involves gradually heating the solution at a temperature of from about −20° C. to about 20° C. over a period of from about 5 hours to about 30 hours, avoiding melt back (liquification) of the solution. A preferred time period for this heating step is from about 5 to about 20 hours, and more preferably, from about 5 to about 10 hours. A preferred temperature for this step is from about −10° C. to about 20° C., and more preferably the temperature is about 0° C. This preferred primary drying cycle reduces the time necessary for the complete lyophilization process. In fact, the preferred primary drying step permits the secondary drying step, in which the polynucleotide solution is heated to a temperature of from about 23° C. to about 27° C., to occur over a period of from about 2 hours to about 3 hours, and provides the lyophilized polynucleotide in a substantially amorphous physical structure which retains at least 90% supercoil over a time period of at least 10 days at about 37° C.

Overall, it is preferable that once vacuum is applied in the steps of this process, it is applied continuously until the last step is completed (i.e., either the second heating or the optional second hold). However, it is possible to vary the vacuum pressure in each heating step as long as the vacuum pressure applied at any time is less than about 200 mTorr.

After the optional final hold is complete, the resulting polynucleotide composition is recovered, which has a water content of from about 0.5 weight percent to about 6 weight percent based on the total weight of the recovered composition. The recovered polynucleotide composition has from about 0.5 to about 6 weight percent, preferably about 1 weight percent to about 5 weight percent, and more preferably from about 2 weight percent to about 4 weight percent water, based on the total weight of the polynucleotide composition. The lyophilized polynucleotide composition preferably contains from about 0.001 parts by weight polynucleotide to about one part by weight polynucleotide per one part by weight cryoprotectant. In one embodiment the polynucleotide composition preferably contains from about 0.001 parts by weight polynucleotide to about 0.5 part by weight polynucleotide per one part by weight cryoprotectant. The polynucleotide composition is preferably amorphous in structure to improve solubility of the composition. Increased solubility is desired to permit relatively quick reconstitution and to make more concentrated compositions.

The following examples illustrate some embodiments of the present invention in detail. These examples are merely illustrative of the present invention and should not be considered as limiting the scope of the invention in any way.

EXAMPLE 1

A Preferred Lyophilized Composition of the Invention

One preferred lyophilized composition of the present invention which uses plasmid DNA as the polynucleotide and sucrose as the cryoprotectant is prepared by the process described above. The DNA plasmid used in these compositions contains the Herpes Simplex Virus gene encoding the $gD_2$ protein linked to a cytomegalovirus promoter and SV40 polyadenlyation site. This plasmid, referred to as plasmid 24, is described in detail in International Patent Application No. WO97/41892, published Nov. 13, 1997 and in FIG. 5D of U.S. Pat. No. 5,593,972.

The components of the pre-lyophilized polynucleotide solution and a liquid control composition are reported in Table 1.

TABLE 1

| Ingredient | Pre-Lyophilized Polynucleotide Solution | Liquid Control Composition |
|---|---|---|
| Plasmid DNA | 0.2% w/v | 0.2% w/v |
| Sucrose | 2.0% w/v | — |
| Phosphate buffer (5 mM) | 0.045% w/v sodium phosphate, monobasic; and 0.047% w/v sodium phosphate, dibasic | — |
| Water for injection (qs) | 100 mL | 100 mL |
| bupivacaine (facilitator) | — | 0.25% w/v |
| EDTA | — | 0.01% w/v |
| citrate buffer | — | 30 mM |
| pH | 6.7 | 6.4 |

The pre-lyophilized solution of Table 1 was subjected to a lyophilization process according to this invention characterized by specific parameters for the freezing, primary drying and secondary drying steps. These parameters are performed in the order presented in Table 2 and include two consecutive primary drying steps and four consecutive secondary drying steps.

TABLE 2

| Lyophilization Cycle | Temperature (° C.) | Vacuum (mTorr) | Time (min) | Ramp/Hold |
|---|---|---|---|---|
| Freezing step | −40 | 200 | 30 | Hold |
| Primary drying steps (2) | 0 | 100 | 30 | Ramp |
| | 0 | 100 | 720 | Hold |
| Secondary drying steps (4) | 30 | 75 | 20 | Ramp |
| | 30 | 75 | 180 | Hold |

TABLE 2-continued

| Lyophilization Cycle | Temperature (° C.) | Vacuum (mTorr) | Time (min) | Ramp/Hold |
|---|---|---|---|---|
| | 25 | 50 | 5 | Ramp |
| | 25 | 50 | 120 | Hold |

The stability of this lyophilized polynucleotide composition and the liquid control at 37° C. were monitored based on decay in % Supercoil (% SC). The samples were analyzed for % SC using the agarose gel method. The agarose gel method is an electrophoretic procedure commonly performed in molecular biology for separation of different forms of DNA. Detection by the agarose gel method relies on the intercalation of the dye ethidium bromide into the DNA. The method utilizes a fluorescent dye binding to the double stranded (ds)-DNA for detection, and the fluorescence is measured indirectly. DNA is electrophoresed on agarose gels containing ethidium bromide (EtBr). Upon intercalation into the DNA, EtBr's fluorescence is strongly enhanced. The fluorescence signal is collected using a CCD (Charge-Coupled Device). The image is integrated (software by Alpha Innotech™) to calculate the relative amounts of open-circular and supercoiled plasmid present in the sample. Results rely on consistent and uniform binding of EtBr to the plasmids. Observations indicate, however, that when % SC is below 93%, the gel method gives artificially low results. For this reason, an alternative HPLC method as described in Montgomery et al, *Pharmsci.*, (suppl. 1998) "*HPLC Assay for Determining Purity of [% Supercoiled] Plasmid DNA in a Vaccine Product*", Abstract 2503 has been developed. The purity of plasmid DNA is assessed by the content of the supercoiled T form. A single hydrolytic step in the phosphodiester linkage of the backbone is enough to convert supercoiled DNA (SC) into the open-circular form (OC). This topological change is reflected in altered mobility on agarose gels. Currently the most commonly used purity assay (% SC assay) for plasmid DNA is the agarose gel based method.

The rate equations describing the degradation of DNA are provided below in Table 3.

TABLE 3

Equation 1   $k_{obs}$ is the observed rate constant and represents overall degradation of DNA (SC = supercoil; OC = open circular)

$$DNA(SC) \xrightarrow{k_{obs}} DNA(OC) \quad \frac{d[DNA]}{dt} = -k_{obs}[DNA]t$$

Equation 2   Under (pseudo) first order conditions, the rate equation for DNA degradation can be written as follows: where, [DNA] is the purity (% SC) or potency of DNA Equation 3   Integration of above equation using the initial conditions, at time t = 0 [DNA] = [DNA]$_0$ results in the following equation:
$\ln[DNA] = \ln[DNA]_0 - k_{obs}t$
Using equation 3 with % SC (purity of DNA) stability data generated at a specific temperature, a plot of ln(% SC) versus time can be generated and $k_{obs}$ can be calculated from the slope of the plot.

TABLE 3-continued

Equation 4 At any given temperature, the shelf-life ($t_{90}$, time to reach 90% SC) can be calculated as follows:

$$t_{90} = \frac{\ln\left(\frac{([\% \ SC]_0)}{(90)}\right)}{k_{obs}}$$

where, [% SC]$_0$ represents purity of DNA at time, t = 0

Equation 5 By assuming [% SC]$_0$ = 95 in equation 4, the shelf-life of plasmid DNA at a given temperature can be calculated as follows:

$$t_{90} = \frac{0.0541}{k_{obs}}$$

Figure 1:
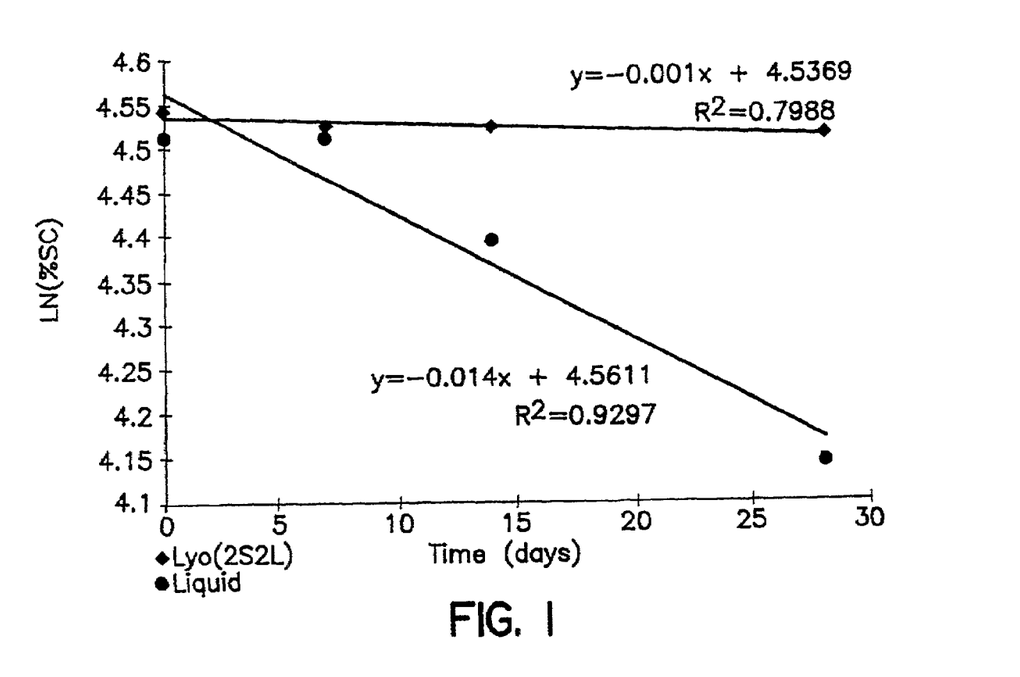
FIG. 1 is a graph plotting the decay in % supercoil ("SC"), i.e., the stability, of lyophilized DNA compositions according to the invention (♦) versus the same DNA in solution (•) over time, using the agarose gel method. Based on Rate Equation 3 in Scheme 1 below, describing the degradation of DNA, plots of ln (% SC) versus time for the preferred lyophilized polynucleotide composition of Example 1 and liquid composition containing plasmid DNA which was not lyophilized (control) were generated. The slopes (−$k_{obs}$, pseudo-first order observed rate constant) of plots were calculated using linear least square regression analysis. For the lyophilized compositions, the slope formula was y=0.001x+4.5369, and the rate constant ($R^2$)=0.7988. For the control the slope formula was y=0.014x+4.5611; and R=0.9297. It can be observed from this figure that the rate constant for preferred lyophilized composition is at least 10-fold lower than the rate constant for liquid composition.

Based on equation 3 in Table 2, plots of ln (% SC) versus time for the above-described lyophilized polynucleotide composition and the control of Table 1 were generated. The results are reported in the graph of FIG. 1. The slopes ($-k_{obs}$, pseudo-first order observed rate constant) of plots were calculated using linear least square regression analysis. FIG. 1 indicates that the rate constant for preferred lyophilized polynucleotide composition is at least 10-fold lower than the rate constant for liquid control composition. These results also indicate that the shelf-life of lyophilized composition is at least 10 times higher than the liquid composition at 37° C. (54 days versus 4 days calculated using equation 5 in scheme 1).

The lyophilized polynucleotide composition of Table 1 was then compared via X-ray diffraction to a DNA solution consisting of the same gD$_2$ gene-containing plasmid DNA as referred to above (0.2% w/v) in citrate buffer at pH6.4, which solution was precipitated using the ethanol precipitation method [Sambrook, J. et al, Molecular Cloning: A Laboratory Manual, 2$^{nd}$ ed., Cold Spring Harbor Laboratory Press, Cold Spring Harbor, N.Y., pp. E10–E11 "*Concentrating Nucleic Acid: Precipitation with Ethanol or Isopropanol*"]. X-ray diffraction patterns were conventionally obtained for both compositions and demonstrated that the lyophilized composition has an X-ray diffraction pattern characteristic of an amorphous structure, while the precipitated DNA produces a diffraction pattern characteristic of a highly crystalline structure. Because the lyophilized polynucleotide compositions of this invention have the physical properties of being amorphous in structure and highly porous, the compositions of this invention are highly soluble water (up to about 20 mg/mL). Solubility tests were performed using a conventional HPLC method.

EXAMPLE 2

A Preferred Lyophilized Composition of the Invention

Another preferred lyophilized composition of the present invention which uses plasmid DNA described in Example 1 as the polynucleotide and trehalose as the cryoprotectant and stabilizer is prepared by the process of this invention. The liquid control was identical to that used in Example 1. Table 4 reports the composition of the pre-lyophilized solution as well as that of the liquid plasmid control.

TABLE 4

| Ingredient | Pre-Lyophilized Polynucleotide Solution | Liquid Control Composition |
|---|---|---|
| Plasmid DNA | 0.2% w/v | 0.2% w/v |
| Trahalose | 2.0% w/v | — |
| Phosphate buffer (5 mM) | 0.045% w/v sodium phosphate, monobasic; and 0.047% w/v sodium phosphate, dibasic | — |
| Water for injection (qs) | 100 mL | 100 mL |
| bupivacaine (facilitator) | — | 0.25% w/v |
| EDTA | — | 0.01% w/v |
| citrate buffer | — | 30 mM |
| pH | 6.7 | 6.4 |

Figure 2:
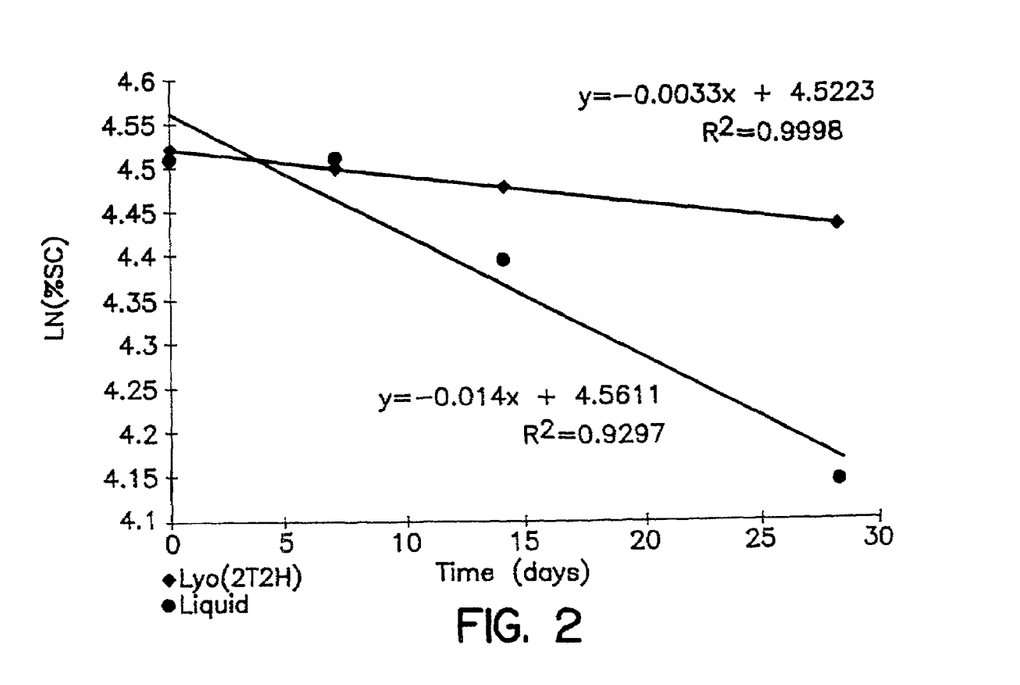
FIG. 2 is a graph similar to that of FIG. 1, but for a preferred lyophilized composition according to the invention (♦) containing plasmid DNA and 2% w/w trehalose as a cryoprotectant with a 4% moisture content (Lyo2T2H) versus the same DNA in non-lyophilized solution (•, Liquid) over time. For the lyophilized composition, the slope formula was y=0.0033x+4.52223, and $R^2$=0.9998. For the control, the slope formula was y=0.014x+4.5611; and $R^2$=0.9297.

The prelyophilized solution Was subjected to the lyophilization process described above in Example 1, and the stability of this composition at 37° C. was monitored based on decay in % Supercoil (SC) as described above in Example 1. The samples were analyzed for %/SC using the agarose gel method. FIG. 2 shows a plot of ln (% SC) versus time for the lyophilized polynucleotide composition and the liquid control composition of Table 4. The slopes ($-k_{obs}$, observed rate constant) from the plots were calculated using linear least square regression analysis, as described in Example 1. The results of FIG. 2 indicate that the rate constant for the lyophilized composition of the present invention is 4-fold lower than the rate constant for the liquid control. This data also indicates that the shelf-life of lyophilized composition of this invention is four times higher than the liquid control at 37° C.

EXAMPLE 3

Screening of Cryoprotectants

Several polynucleotide solutions containing plasmid DNA with different cryoprotectants (sucrose, trehalose, PVP and sorbitol) were lyophilized according to the present invention. The plasmid DNA used in these experiments was the same plasmid which expresses the gD$_2$ antigen of Herpes Simplex Virus, type 2, as employed in Example 1.

Table 5 presents the compositions of the eight pre-lyophilized polynucleotide solutions evaluated. The lyophilization parameters were the same as those described in Table 2 for Example 1. The % SC was measured using the agarose gel method as described above in Example 1 both before and after lyophilization of these solutions according to this invention. Thus, Table 5 also provides the % SC pre-lyophilization for each polynucleotide solution and the % SC post-lyophilization for each polynucleotide composition lyophilized according to this invention.

TABLE 5

| Component or Characteristic | Polynucleotide Solution | | | | | | | |
|---|---|---|---|---|---|---|---|---|
| | 1 | 2 | 3 | 4 | 5 | 6 | 7 | 8 |
| Plasmid DNA (mg/mL) | 1.1 | 1.1 | 1.1 | 1.1 | 1.1 | 1.1 | 1.1 | 1.1 |
| Trehalose (% w/v) | 2 | — | — | — | — | — | — | — |
| PVP (% w/v) | — | 5 | — | — | — | — | — | — |
| Sucrose (% w/v) | — | — | 2 | 2 | — | — | 2 | — |
| Sorbitol (% w/v) | — | — | — | — | 5 | — | — | — |
| Phosphate buffer (mM) | 10 | 10 | 10 | 10 | 10 | 10 | — | — |
| Citrate buffer (mM) | — | — | — | — | — | — | 10 | 10 |
| EDTA (%) | — | — | — | 0.01 | — | — | — | — |
| Water for injection (qs) | 100 mL | 100 mL | 100 mL | 100 mL | 100 mL | 100 mL | 100 mL | 100 mL |
| pH | 6.9 ± 0.2 | 6.9 ± 0.2 | 6.9 ± 0.2 | 6.9 ± 0.2 | 6.9 ± 0.2 | 6.9 ± 0.2 | 6.9 ± 0.2 | 6.9 ± 0.2 |
| Moisture content (%) post-lyo | 1-2% | >>1% | 1-2% | 1-2% | 1-2% | 1-2% | 1-2% | 1-2% |
| % SC prelyophilization | 96.8 ± 0.7 | 96.8 ± 0.7 | 96.8 ± 0.7 | 96.8 ± 0.7 | 96.8 ± 0.7 | 96.8 ± 0.7 | 96.4 ± 0.6 | 96.4 ± 0.6 |
| % SC postlyophilization | 93.8 ± 0.7 | 81.2 ± 0.7 | 92.0 ± 0.2 | 92.7 ± 0.6 | 92.4 ± 0.7 | 66.1 ± 1.0 | 92.7 ± 1.0 | 90.7 ± 0.9 |

Based on these results, trehalose and sucrose are more effective cryoprotectants than PVP and sorbitol. In the absence of cryoprotectants, the lyophilized phosphate buffer control based on the lyophilization of solution 6 according to this invention showed more than 30% loss in percent supercoil and lyophilized citrate buffer control based on the lyophilization of solution 8 showed less than 5% loss. This could be attributed to the possible pH drift towards acidic pH in the phosphate sample due to freezing of crystalline dibasic species before the amorphous monobasic species. However, this phenomena was not observed in the lyophilized polynucleotide compositions in the presence of cryoprotectant, sucrose (see solutions 3 and 7). Therefore, in the presence of cryoprotectant, the buffer species does not show any effect on the lyophilized polynucleotide composition.

The moisture results for the lyophilized polynucleotide compositions indicate that PVP did not show good cryoprotectant properties because the lyophilized compositions containing PVP were almost dried (moisture<<1%) when compared to the lyophilized compositions containing other cryoprotectants (moisture content 1-2%). The PVP-containing lyophilized compositions also showed more than 15% loss in percent supercoil. According to this data, sucrose and trehalose are good cryoprotectants for the lyophilized plasmid DNA compositions according to this invention.

EXAMPLE 4

Effect of the Lyophilized Compositions of the Invention on the Immune Response To assess the utility of lyophilized polynucleotide compositions of this invention as pharmaceutical or research reagents, the effect of lyophilized polynucleotide compositions and controls on immune responses was evaluated using the lyophilized compositions prepared as described in Example 3 above.

One control for the lyophilized compositions was the prelyophilized polynucleotide solution No. 6 of Table 5 containing no cryoprotectant (Phos Pre-Lyo). Another control used in these experiments was the lyophilized citrate buffer composition of solution No. 8 of Table 5 containing no cryoprotectant (Citrate Post-Lyo). The lyophilized compositions of the invention which was evaluated in this experiment were the lyophilized polynucleotide solution No. 1 of Table 5 with trahalose as a cryoprotectant in phosphate buffer (Trahalose/Phos); lyophilized polynucleotide solution No. 3 of Table 5 with sucrose as a cryoprotectant in phosphate buffer (Sucrose/Phos); and lyophilized polynucleotide solution No. 7 with sucrose as a cryoprotectant in citrate buffer (Sucrose/Cit). The controls of FIGS. 3 and 4 (023 control and negative control) are identical and contain the plasmid backbone without the $gD_2$ sequence and buffer.

Each lyophilized composition was reconstituted in either phosphate or citrate buffer solution, whichever was used in the original pre-lyophilization solution. Balb/C mice (5 per group) were immunized by the intramuscular route with 50 µg/dose of DNA in a 100 µL volume of each reconstituted lyophilized composition of Example 3. No other component was added to these compositions. After three weeks the animals were euthanized.

A. Cellular Immune Response Evaluation

Spleens were removed from the mice described above and used to determine antigen-specific cellular immune responses using a lymphoproliferation assay. Single cell suspensions were prepared from the harvested spleens and these cells were then cultures at $2 \times 10^5$ cells/well in the absence or presence of 20 ng/mL of purified $gD_2$ protein. Cultures were incubated at 37° C. in 5% $CO_2$ for four days before adding 20 µLs of complete RPMI-1640 media containing 1 µCi of $^3[H]$ thymidine (ICN Inc., Costa Mesa, Ca) to each well and incubating for an additional 18 hours. The cells were harvested onto glass fiber mats using a multiple sample harvester and the incorporation of radioactivity was measured using conventional liquid scintillation procedures in a beta counter (Wallac, Finland).

B. Humoral Immune Response Evaluation

Serum samples were collected for analysis of antibody (humoral) response to HSV $gD_2$. The $gD_2$ specific IgG antibodies in serum were assayed by an ELISA. Briefly, 96 well flat bottom plates (Co-star, Cambridge, Mass.) were coated overnight at 4° C. with purified $gD_2$ protein at a concentration of 0.4 μg/mL. The plates were washed three times with phosphate buffered saline (PBS) and blocked with 4% bovine serum albumin (BSA) for one hour at room temperature. Fifty μLs of the appropriate dilution of serum were then added to the plate and left overnight at 4° C. After washing with BPST five times, a 1:2000 dilution of peroxidase conjugated anti-mouse IgG (Sigma, St. Louis, Mo.) was added and the plates incubated for one hour. The plates were washed with PBST before adding the substrate 3,3',5,5'-tetramethylbenzidine (TMB)-$H_2O_2$ (Biotecx, Houston, Tx). Color was allowed to develop for 30 minutes before reading at 450 nm on an $E_{max}$ microplate reader (Molecular Devices, Sunnyvale, Calif.)

C. Results

Figure 3:
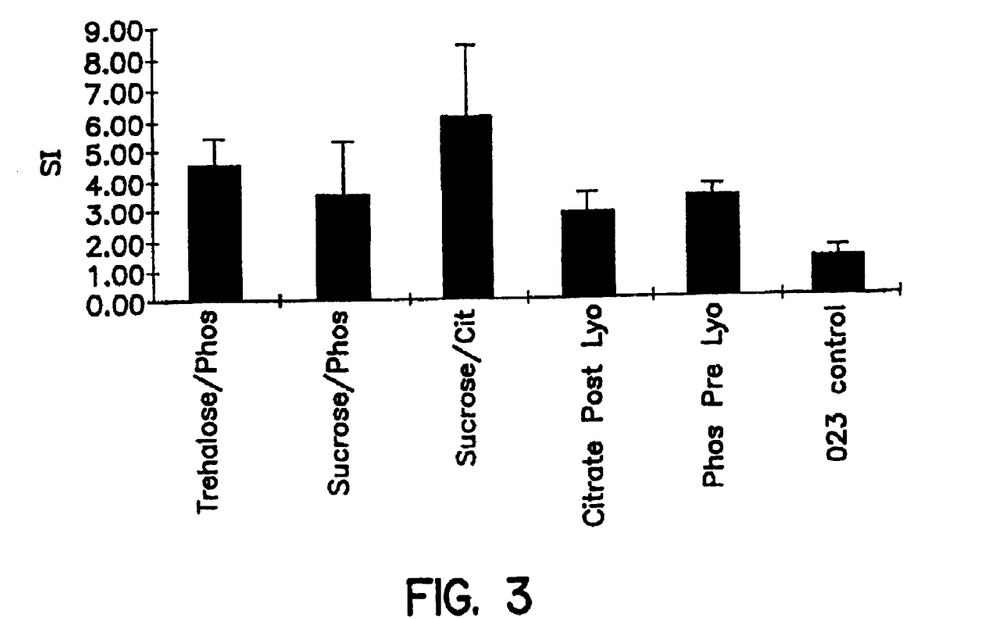
FIG. 3 is a bar graph which illustrates antigen-specific cellular immune responses in Balb/C mice to lyophilized DNA compositions (plasmids containing the Herpes Simplex Virus gene encoding the $gD_2$ protein) of this invention and to controls. One control was the prelyophilized polynucleotide solution No. 6 of Table 4 in Example 3 below, containing no cryoprotectant (Phos Pre-Lyo). Another control was the lyophilized citrate buffer composition of solution No. 8 of Table 4 containing no cryoprotectant (Citrate Post-Lyo). The "023 control" is a prelyophilized solution wherein the DNA is the same plasmid backbone as used in the other compositions, but with no $gD_2$ sequence. The lyophilized compositions of the invention which were employed included the lyophilized polynucleotide solution No. 1 of Table 4 with trahalose as a cryoprotectant in phosphate buffer (Trahalose/Phos); lyophilized polynucleotide solution No. 3 of Table 4 with sucrose as a cryoprotectant in phosphate buffer (Sucrose/Phos); and lyophilized polynucleotide solution No. 7 with sucrose as a cryoprotectant in citrate buffer (Sucrose/Cit). The effects of each polynucleotide composition on the cellular immune response was measured by a lymphoproliferation assay described in Example 4, and reported as Stimulation Index (SI).
Figure 4:
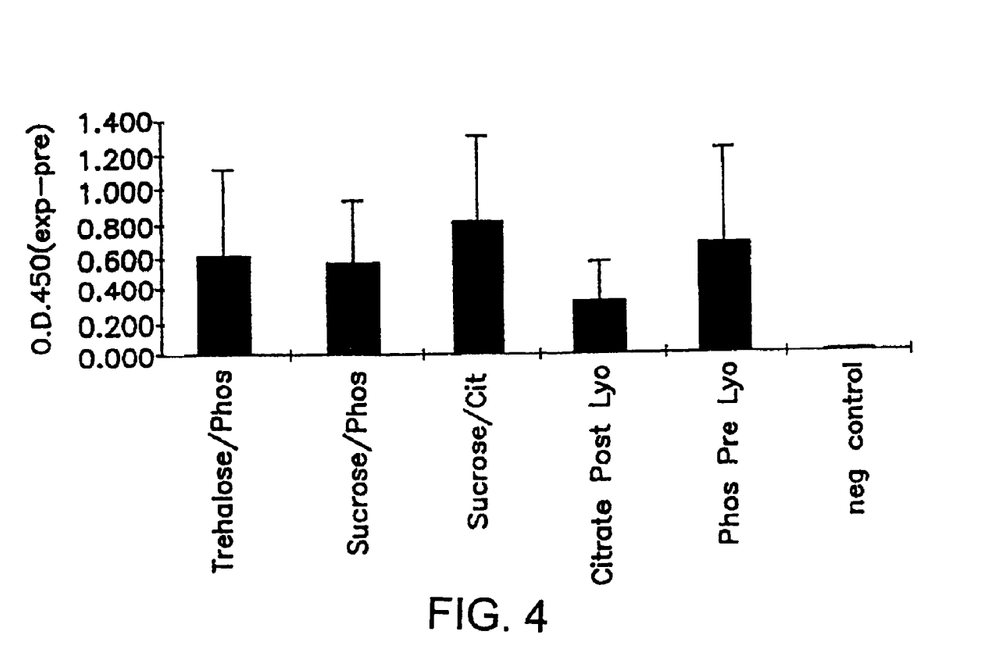
FIG. 4 is a bar graph showing the humoral (antibody) response measured in optical density (OD) at 450 nm in serum of individual Balb-C mice to the lyophilized DNA compositions of this invention and controls identified in FIG. 3. The negative control and the 023 control are identical. The effects of each polynucleotide composition on the humoral immune response was measured by standard ELISA as described below in Example 4.

FIGS. 3 and 4 represent the cellular and humoral responses for the above-identified compositions; respectively. The results indicate higher cellular and humoral responses for the lyophilized citrate/sucrose composition of the present invention compared to lyophilized phosphate/citrate composition of the present invention and to the lyophilized citrate/no cryoprotectant control. Comparing the results for lyophilized compositions of this invention to the pre-lyophilized control in phosphate buffer, it is clear that the lyophilization process and the inclusion of cryoprotectants (sucrose or trehalose) in the polynucleotide compositions according to this invention does not adversely effect the cellular and humoral responses. The lyophilized compositions of this invention retain the activity of plasmid or polynucleotide contained therein.

EXAMPLE 5

Evaluation of Lyophilized Compositions of the Invention

Sixteen different pre-lyophilized solutions were evaluated and are described in Table 6. The DNA in each solution used was the same $gD_2$-containing plasmid described in Example 1. These solutions are identified by different codes in the table, and differ in the DNA concentration (represented by the first number in the composition code), the identity of the cryoprotectant (represented by the first letter in the code), the cryoprotectant concentration (represented by the second number in the code), and the moisture content after lyophilization (represented as low, L, or high, H, in the code). The pre-lyophilized solutions were made with water for injection of qs 100 mL, and were lyophilized according to this invention using the lyophilization cycle parameters as outlined in Table 2 above.

All of the lyophilized compositions of Table 6 were subjected to accelerated stability testing at 37° C., as was the liquid control (composition code # 96F0254), which has the formula of the liquid control reported in Table 1 of Example 1 with 1 mg/mL plasmid DNA. The stability study also included a lyophilized plasmid composition without cryoprotectant as another control. Samples were collected at different time intervals from day 0 to day 30 and analyzed for % SC using the agarose gel method as described in Example 1. Using the % SC data in least square regression analysis (see Equation 3 in Table 3), pseudo-first order rate constants ($k_{obs}$) for the degradation of DNA in the different compositions were calculated. The $k_{obs}$ values with 95% confidence intervals (CI) and $R^2$ (goodness of fit) values for different compositions are also summarized in Table 6.

TABLE 6

| Comp. Code # | DNA (mg/mL) | Cryo-protectant (% w/w) | Moist. content post-lyo (%) | $K_{obs}$ (95% C.I. ($\times 10^{-4}$) day$^{-1}$ post-lyophilization | $R^2$ post-lyophilization |
|---|---|---|---|---|---|
| 96F-0254 | 1 | — | — | 139.8 ± 117 | 0.93 |
| 1S1L | 1 | sucrose 1% | 2 | 12.3 ± 20.39 | 0.77 |
| 1S2L | 1 | sucrose 2% | 2 | 4.0 ± 6.7 | 0.77 |
| 1T1L | 1 | trahalose 1% | 2 | 66.5 ± 46.2 | 0.95 |
| 1T2L | 1 | trahalose 2% | 2 | 94.1 ± 28.9 | 0.99 |
| 2S1L | 2 | sucrose 1% | 2 | 11.2 ± 8.6 | 0.94 |
| 2S2L | 2 | sucrose 2% | 2 | 10.2 ± 15.5 | 0.80 |
| 2T1L | 2 | trahalose 1% | 2 | 40.5 ± 28.2 | 0.95 |
| 2T2L | 2 | trahalose 2% | 2 | 55.0 ± 7.6 | 1.00 |
| 1S1H | 1 | sucrose 1% | 4 | 18.9 ± 43.1 | 0.64 |
| 1S2H | 1 | sucrose 2% | 4 | 3.1 ± 10 | 0.47 |
| 1T1H | 1 | trahalose 1% | 4 | 48.5 ± 24.9 | 0.97 |
| 1T2H | 1 | trahalose 2% | 4 | 41.9 ± 41 | 0.91 |
| 2S1H | 2 | sucrose 1% | 4 | 6.1 ± 20 | 0.47 |
| 2S2H | 2 | sucrose 2% | 4 | 21.6 ± 19.2 | 0.92 |
| 2TH1 | 2 | trahalose 1% | 4 | 26.1 ± 20.1 | 0.94 |
| 2T2H | 2 | trahalose 2% | 4 | 32.5 ± 1.4 | 1.00 |

The % SC results indicated that all sucrose-containing lyophilized compositions of the invention are stable at 37° C. for at least 4 weeks (i.e., the duration of the experiment). It is clear from the pseudo-first order rate constants ($k_{obs}$) with 95% confidence intervals (CI) and $R^2$ (goodness of fit) values reported in Table 5 that the $k_{obs}$ for the current clinical composition is at least 10 times higher than the $k_{obs}$ for most of the lyophilized polynucleotide compositions of this invention containing sucrose as a cryoprotectant. Similarly, the $k_{obs}$ for the current clinical composition is at least 1.5 times greater than the $k_{obs}$ for the lyophilized polynucleotide compositions of this invention containing trehalose as a cryoprotectant. Based on this data, sucrose is the best cryoprotectant as well as the best stabilizing agent for lyophilized polynucleotide compositions of this invention.

The shelf-life (% supercoil from 95% to 90%) of the lyophilized composition containing sucrose (Code 2S2L) is 54 days at 37° C., compared to 4 days of shelf-life for the liquid composition Code 96F0254. At 5° C., however, this current clinical composition is stable for two years. Therefore, by extrapolation, the lyophilized composition of this invention would be expected to have a very long shelf life. At ambient temperature (25° C.), a stability of at least six months is expected. High moisture, lyophilized compositions of this invention containing trehalose as the cryoprotectant showed better stability compared to similar low moisture compositions containing trahalose.

The rate constants for low moisture lyophilized compositions of this, invention containing sucrose are relatively lower compared to high moisture, lyophilized compositions of this invention containing sucrose. Based on this data, the lyophilized composition of Example 1 (containing 2% sucrose) was selected as the preferred composition for the next experiment.

EXAMPLE 6

High Concentration DNA Product

A preferred lyophilized composition of the invention is provided to lyophilize bulk DNA for the preparation of a final high concentration drug product also containing a facilitator. This composition contains the same plasmid DNA as described in Example 1 at a concentration of 0.2% w/v in the pre-lyophilized solution, sucrose as a cryoprotectant at a concentration of 2.0% w/v, citrate buffer (5 mM, pH 6.7) and 100 mL of water for injection qs. The composition was lyophilized using the cycle outlined in Example 1, Table 2 above. Different concentrations of bupivacaine, a facilitator (0.25, 0.6 and 1.0% w/v) were prepared in citrate buffer (5 mM, pH 6.7) and used to reconstitute the above-described lyophilized product. To obtain desired DNA concentrations, different amounts of the buffered bupivacaine solutions were added to the lyophilized powder. The resulting "drug" formulations are described in Table 7, which also reports the stability of the high concentration DNA product as time in days after reconstitution as measured in % SC, as above described.

TABLE 7

| Composition # | DNA Concentration (mg/mL) | Bupivacaine Concentration (% w/v) | Time (days) | Purity (% SC) |
|---|---|---|---|---|
| 1 | 5.3 | — | 0 | 95 |
|   |     |   | 18 | 92 |
| 2 | 5.3 | 0.6 | 0 | 95 |
|   |     |     | 18 | 93 |
| 3 | 10 | 1.0 | 0 | 95 |
|   |    |     | 1 | 95 |
|   |    |     | 3 | 95 |
| 4 | 10 | — | 0 | 95 |
|   |    |   | 18 | 94 |
| 5 | 20 | — | 0 | 95 |
|   |    |   | 18 | 93 |

It can be observed from these results that at least up to 20 mg/mL of the reconstituted lyophilized polynucleotide compositions of this invention is stable for 18 days based on purity. It should also be noted that the reconstituted solutions were uniform based on physical appearance.

All references and patents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for preparing a lyophilized polynucleotide composition comprising the steps of:
   (a) forming an aqueous plasmid DNA solution having a pH of from about 6.2 to about 7.8 and comprising from about 0.1 mg/mL to about 5 mg/mL of at least one plasmid DNA based on the total volume of said plasmid DNA solution, and from about 0.5 weight percent to about 10 weight percent of at least one carbohydrate cryoprotectant, based on the total weight of said plasmid DNA solution;
   (b) cooling said plasmid DNA solution to a temperature of from about −30° C. to about −70° C., until frozen;
   (c) applying vacuum to reduce the pressure to about 25 mTorr to about 250 mTorr;
   (d) gradually heating said plasmid DNA solution a first time to a temperature of from about −40° C. to about 20° C. over a period of from about 5 hours to about 40 hours;
   (e) holding said plasmid DNA solution after heating step (d), at a temperature of from about −35° C. to about 10° C. and at a pressure of from about 25 mTorr to about 250 mTorr for a period of from about 1 hour to about 10 hours;
   (f) drying the plasmid DNA solution by gradually heating said solution after the holding step (e), to a temperature of from about 20° C. to about 30° C. over a period of from about 1 hour to about 20 hours and at a pressure of from about 25 mTorr to about 150 mTorr; and
   (g) recovering the lyophilized composition having water content of from about 0.5 weight percent to about 6 weight percent based on the total weight of said recovered composition.

2. The method according to claim 1, wherein said plasmid DNA solution of step (a) further comprises a buffer.

3. The method according to claim 1 further comprising after step (f), the step of holding the plasmid DNA solution at a temperature of from about 20° C. to about 30° C. and at a pressure of from 25 mTorr to about 150 mTorr for a period of from about 1 hour to about 10 hours.

4. The method according to claim 1 wherein during cooling step (b), said plasmid DNA solution is gradually cooled to a temperature of from about −30° C. to about −70° C. over a period of from about 1 hour to about 5 hours.

5. The method according to claim 1 wherein between steps (c) and (d), said plasmid DNA solution is held at a temperature of step (b) and pressure of step (c) for about 0.5 to about 5 hours.

6. The method according to claim 1 wherein during heating step (d), the pressure is from about 40 mTorr to about 150 mTorr.

7. The method according to claim 1, wherein heating step (d) is over a period of from about 7 hours to about 11 hours, holding step (e) is for a period of about 1 hour, and heating step (f) is over a period of about 2 hours.

8. The method of claim 1, wherein the plasmid DNA encodes a protein from a pathogen.

9. The method according to claim 1, wherein the cryoprotectant is a simple or complex carbohydrate.

10. The method according to claim 9, wherein the carbohydrate cryoprotectant is selected from the group consisting of an aldose, a ketose, an amino sugar, a disaccharide, a polysaccharide, and combinations thereof.

11. The method according to claim 10, wherein the carbohydrate cryoprotectant is selected from sucrose, glucose, lactose, trehalose, arabinose, pentose, ribose, xylose, galactose, hexose, idose, monnose, talose, heptose, fructose, gluconic acid, sorbitol, mannitol, methyl α-glucopyranoside, maltose, isoascorbic acid, ascorbic acid, lactone, sorbose, glucaric acid, erythrose, threose, arabinose, allose, altrose, gulose, erythrulose, ribulose, xylulose, psicose, tagatose, glucuronic acid, gluconic acid, glucaric acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, starch and combinations thereof.

12. The method according to claim 11 wherein said carbohydrate cryoprotectant is selected from the group consisting of sucrose, glucose, lactose, trehalose, and combinations thereof.

13. The method according to claim 12 wherein the cryoprotectant is sucrose.

14. The method according to claim 1, which further comprises a combination of two or more cryoprotectants.

15. The method according to claim 1 wherein the composition generated by the method has a predominantly amorphous physical structure and retains at least 90% supercoil over a time period of at least 10 days at about 37° C.

16. The method according to claim 1, wherein said water content is from about 1 weight percent to about 5 weight percent.

17. The method of claim 8, wherein said pathogen is selected from the group consisting of alpha virus, adenovirus, vaccinia virus, retrovirus, adeno-associated virus, herpes virus, polio virus, delta virus and viroids.

18. An improved method for lyophilizing a polynucleotide composition, said method comprising freezing said composition, subjecting said frozen composition to a vacuum, performing a primary drying step, increasing the pressure on the composition following the drying step, performing a secondary drying step, and recovering a lyophilized product, the improvement comprising the step of: subjecting a plasmid DNA solution containing a carbohydrate cryoprotectant, which solution has been cooled until frozen and subjected to a vacuum, to a primary drying cycle comprising gradually heating said solution at a temperature of from about −20° C. to about 20° C. over a period of from about 5 hours to about 30 hours and avoiding melt back of said solution, wherein said primary drying cycle reduces the time necessary for the complete lyophilization process and provides the lyophilized polynucleotide composition in an amorphous physical structure which retains at least 90% supercoil over a time period of at least 10 days at about 37° C.

19. The method according to claim 18, wherein said primary drying cycle time period is from about 5 to about 20 hours.

20. The method according to claim 18, wherein said primary drying cycle temperature is from about −10° C. to about 20° C.

21. The method according to claim 18 further comprising a secondary drying step, in which the plasmid DNA solution is heated to a temperature of from about 23° C. to about 27° C. over a period of from about 2 hours to about 3 hours.

22. The method according to claim 18, wherein the cryoprotectant is a simple or complex carbohydrate.

23. The method according to claim 22, wherein the carbohydrate cryoprotectant is selected from the group consisting of an aldose, a ketose, an amino sugar, a disaccharide, a polysaccharide, and combinations thereof.

24. The method according to claim 22, wherein the carbohydrate cryoprotectant is selected from sucrose, glucose, lactose, trehalose, arabinose, pentose, ribose, xylose, galactose, hexose, idose, monnose, talose, heptose, fructose, gluconic acid, sorbitol, mannitol, methyl α-glucopyranoside, maltose, isoascorbic acid, ascorbic acid, lactone, sorbose, glucaric acid, erythrose, threose, arabinose, allose, altrose, gulose, erythrulose, ribulose, xylulose, psicose, tagatose, glucuronic acid, gluconic acid, glucaric acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, starch and combinations thereof.

25. The method according to claim 24, wherein said carbohydrate cryoprotectant is selected from the group consisting of sucrose, glucose, lactose, trehalose, and combinations thereof.

26. The method according to claim 25, wherein the cryoprotectant is sucrose.

27. The method according to claim 18, which further comprises a combination of two or more cryoprotectants.

28. The method according to claim 18, wherein the composition generated by the method has a predominantly amorphous physical structure and retains at least 90% supercoil over a time period of at least 10 days at about 37° C.

* * * * *